United States Patent [19]

Robertson et al.

[11] 4,341,728
[45] Jul. 27, 1982

[54] METHOD FOR MAKING AN IUD WITH SHRINKING OF A MEDICATED ATTACHMENT ONTO A SUPPORT

[75] Inventors: Dale N. Robertson, Scotch Plains, N.J.; John Braun, Westbury, N.Y.

[73] Assignee: The Population Council, Inc., New York, N.Y.

[21] Appl. No.: 105,858

[22] Filed: Dec. 20, 1979

[51] Int. Cl.³ .................. B29C 5/00; B29C 27/00; B29D 3/00
[52] U.S. Cl. .................................. 264/161; 264/238; 264/342 R
[58] Field of Search .................... 128/130, 131; 264/342 R, 230, 289.3, 229, 249, 250, 259, 297, 349, 232, 161, 238, 219, 234; 424/15, 22, 28; 156/86

[56] References Cited

U.S. PATENT DOCUMENTS

| 1,537,860 | 5/1925 | Miller | 18/55 |
|---|---|---|---|
| 1,543,506 | 6/1925 | Miller | 18/55 |
| 2,041,424 | 5/1936 | McCormick et al. | 128/131 |
| 2,945,263 | 7/1960 | Leistensnider | 18/55 |
| 3,163,692 | 12/1964 | Smith et al. | 264/249 |
| 3,279,996 | 10/1966 | Long, Jr. et al. | 167/82 |
| 3,415,916 | 12/1968 | Valvi | 264/297 |
| 3,443,006 | 5/1969 | Simons et al. | 264/249 |
| 3,549,789 | 12/1970 | Haroldson | 174/122 |
| 3,710,795 | 1/1973 | Higuchi et al. | 128/260 |
| 3,777,015 | 12/1973 | Zaffaroni | 424/15 |
| 3,825,643 | 7/1974 | Hiller et al. | 264/161 |
| 3,832,252 | 8/1974 | Higuchi et al. | 156/86 |
| 3,888,975 | 6/1975 | Ramwell | 128/130 |
| 3,914,370 | 10/1975 | Lloyd et al. | 264/297 |
| 3,993,073 | 11/1976 | Zaffaroni | 128/260 |
| 3,996,933 | 12/1976 | Gotnick | 128/130 |
| 4,012,496 | 3/1977 | Schöpflin et al. | 424/15 |
| 4,012,497 | 3/1977 | Schöpflin | 424/22 |
| 4,031,202 | 6/1977 | Laughlin et al. | 424/28 |
| 4,038,978 | 8/1977 | Morris et al. | 128/130 |
| 4,169,069 | 9/1979 | Unger et al. | 424/19 |
| 4,188,951 | 2/1980 | Higuchi et al. | 128/260 |
| 4,292,965 | 10/1981 | Nash et al. | 128/260 |

OTHER PUBLICATIONS

Henzl et al., Am. J. Obstet Gynecol., 117:101–106, 1973.
Mishell; D. R., Jr. et al., Clinical Performance and Endocrine Profiles with Contraceptive Vaginal Rings Containing a Combination of Estradiol and d-Norgestrel, Am. J. Obstet Gynecol, 130:55, (1978).
El-Mahgoub, D-Norgestrel Slow-Releasing T Device as an Intrauterine Contraceptive, Sep. '75, pp. 133–138, Am. J. Obstet. Gynecol.

Primary Examiner—Willard E. Hoag
Attorney, Agent, or Firm—Brumbaugh, Graves, Donohue & Raymond

[57] ABSTRACT

Method for making a medicated IUD including a preexisting contraceptive intrauterine platform and an attachment formed as a cylindrical sleeve of base polymer containing a drug such as an antifertility agent. Local controlled release administration of the drug is added to the contraceptive effect of the preexisting platform. The IUD attachment can be made by centrifuging a medical grade of RTV silicone rubber to remove reinforcing fillers therefrom. A selected quantity of the drug is mixed into the fillerless silicone rubber, and the drug and silicone mixture is injected into a multicavity mold. After the mixture sets and the sleeves are removed from the mold, the sleeves are trimmed, then swollen by immersion in a solvent, and slipped onto a stem of the chosen IUD to shrink about the stem. An outer covering over the sleeve can control the drug release rate and impart greater strength to the fillerless silicone rubber of the attachment. The outer covering can be a tube likewise swollen and slipped onto the sleeve to tightly shrink thereon. The multicavity mold has two clamped-together plates with aligned half cavities, an injection opening adapted to fit an injection syringe and alignment grooves to hold tubes or pins that form the axial openings through the sleeves.

13 Claims, 5 Drawing Figures

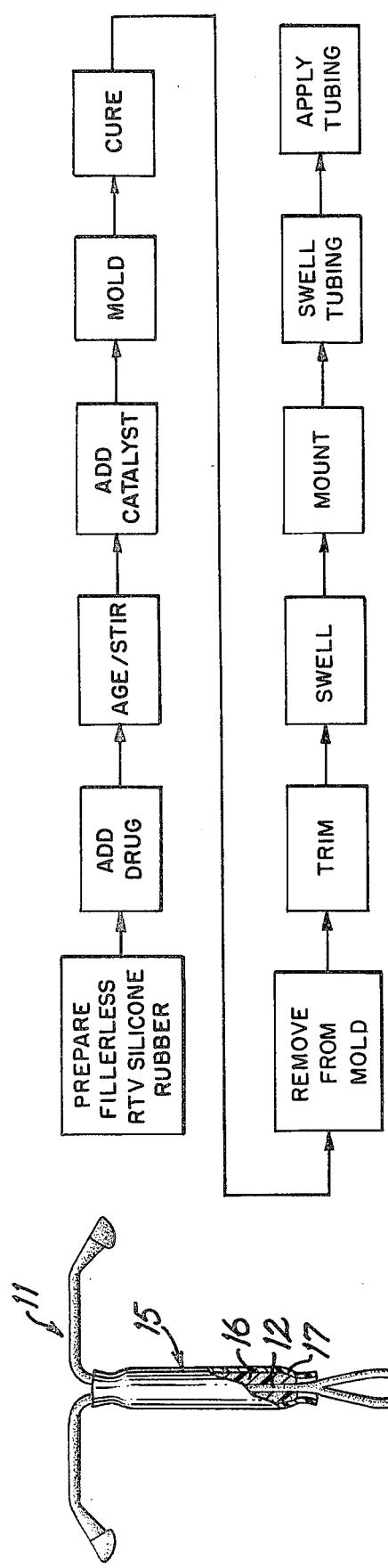
FIG. 1
FIG. 2
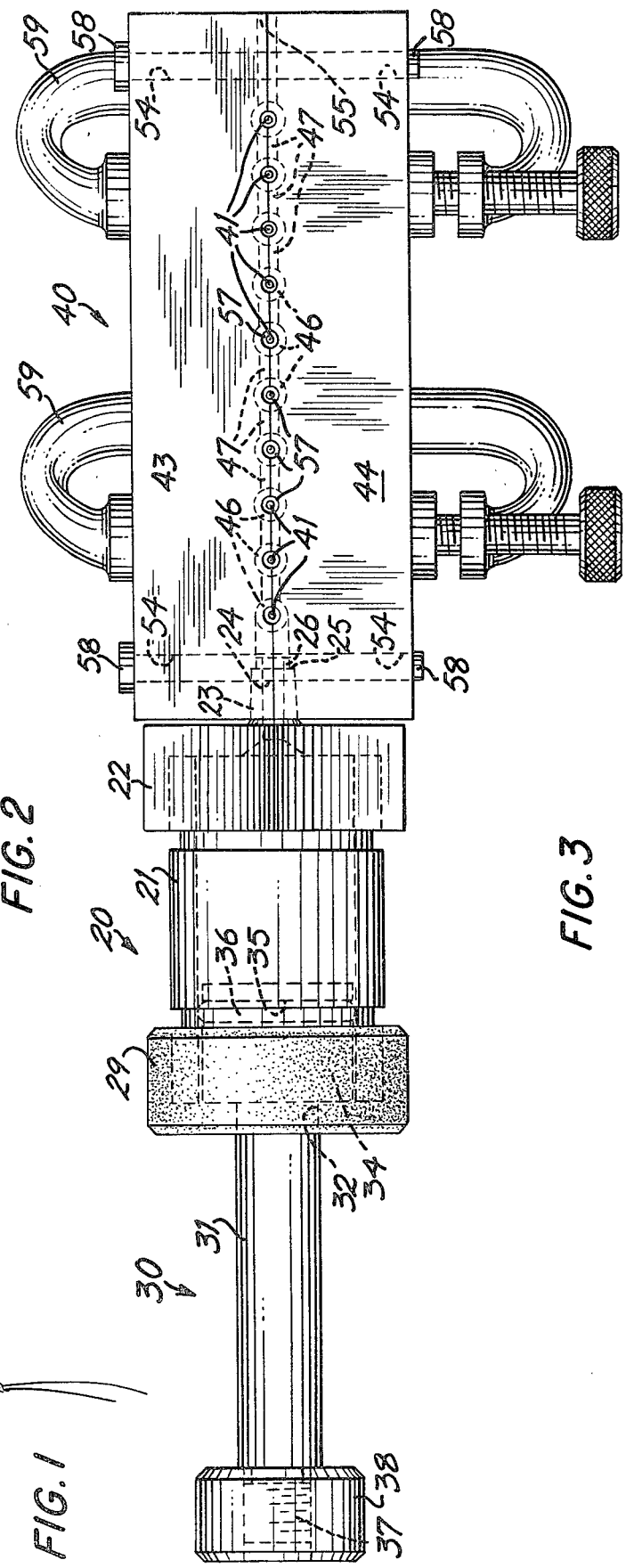
FIG. 3

METHOD FOR MAKING AN IUD WITH SHRINKING OF A MEDICATED ATTACHMENT ONTO A SUPPORT

BACKGROUND OF THE INVENTION

This invention relates to intrauterine drug delivery devices. More particularly, the invention relates to drug delivery attachments for an intrauterine device (IUD) that is an existing, substantially stable, nonmedicated platform, and to methods and apparatus for making and applying the attachments.

Intrauterine devices are known that provide a system for timed release, local administration of drug. For example, IUD's having a drug-releasing erodible outer layer or partial covering have been suggested for delivering a drug to the uterus. In one example of the foregoing, it has been suggested that a small section of a Lippes loop be coated with drug distributed in an erodible polymer. In another example, a sleeve of bioerodible material, having a contraction inducing drug distributed therein, is attached to an IUD that is not a stable platform, but is especially constructed to deteriorate and be expelled.

IUD's partly or entirely formed with medicament-containing silicone rubber have been suggested to provide timed release of the drug in utero. In one example, an IUD includes a tube enclosing a drug and closed by silicone rubber for release of the drug through the silicone rubber. In another example, a resilient, stainless steel member is entirely encased within silicone rubber which can carry a progestogen. In this case, the internal stainless steel member is a flexible, wirelike device that permits the IUD to be collapsed for insertion and to flex to a normal, expanded condition when in place. On the other hand, hollow IUD's containing contraceptive drugs are known. Inside, these contain the drug in a solid or liquid medium. The drug release rate is controlled by the drug permeable walls of the device. A large number of materials for the walls of such devices have been proposed and these include silicone rubbers. Other IUD's of both room temperature and low temperature vulcanizing silicone rubbers with a contraceptive drug distributed therein have been described.

Because room temperature vulcanizing (RTV) silicone rubbers have been found to lack strength necessary in many applications, fillers are added for reinforcement. The fillers in RTV silicones have been determined to be undesirable in drug release articles, however. The fillers, it is said, adversely affect the release of the drug. For this reason, the low temperature vulcanizing (LTV) silicone rubbers have been recommended for the base or carrier material in drug release devices.

BRIEF SUMMARY OF THE INVENTION

According to this invention, an intrauterine controlled release drug delivery article is associated with a proven IUD platform. The drug release article is constructed for attachment to the platform, which is nonmedicated and relatively stable and can be of a proven design. The attachment can be a molded sleeve tightly secured on a stem of an extant IUD.

In a preferred embodiment, an outer drug permeable tube surrounds the sleeve, controlling the rate of administration of the drug contained in the sleeve. RTV silicone rubbers can be employed as the base or carrier material of the sleeve. Removal of the fillers from commercially available silicone rubber, for example by centrifuging, makes the silicone rubber more satisfactory for drug release. The use of the outer tube in tightly fitting relation over the sleeve can impart structural integrity to the fillerless silicone rubber of the attachment to permit it to be handled in an ordinary way prior to insertion without deterioration.

The method of manufacturing the attachment and securing it on the extent IUD provides an easy to use series of steps wherein multiple attachments can be molded and securely fitted onto IUD stems. There is no need to specially manufacture the platform or to adapt it specially for drug release. Silicone rubber, such as the aforementioned fillerless RTV silicone, can be mixed with the drug and molded in a multicavity mold to form the sleeves. The sleeves are then swollen in a solvent, and slipped onto the IUD stem. There they contract tightly about the IUD stem.

The process can include the steps of centrifuging commercially available RTV silicone rubber to remove the fillers and placing over the sleeve a drug permeable covering such as the above-mentioned length of silicone rubber tubing. The outer tubing that insures structural integrity of the fillerless RTV, while helping to control the dosage, can, likewise, be swollen in a solvent, slipped onto the drug-containing sleeve, and permitted to shrink tightly thereabout. With the sleeve and tubing tightly fitted onto the stem, the attachment will withstand normal handling that would otherwise be impermissible for fillerless RTV silicone rubber articles.

The apparatus for making the drug-containing sleeves includes a multicavity mold that facilitates the molding of multiple IUD attachments simply and for easy removal for application to an available platform. The mold includes a pair of plates with aligning recesses. With the plates clamped together, the recesses combine to form the multiple cavities of the mold. Inserts extend into these cavities to form the central openings through the sleeves. Grooves in the mold plates correctly locate the inserts centrally with respect to the multiple cavities. The cavity sizes can be chosen to provide a sleeve with dimensions that give the desired drug release rate.

For injection of the viscous silicone rubber and drug mixture, a special syringe is provided with an injection nipple or projection matching and mating with an injection opening in the mold. The syringe and mold plates are sufficiently heavy duty to withstand the pressures needed to move the viscous silicone rubber into the mold. Once the silicone rubber has set, the mold plates are separated, the multiple sleeves are removed, and the interconnecting branches formed in the mold passages from sleeve to sleeve are separated and discarded. The sleeves are then ready for swelling and placement on the IUD stem.

Because the drug release sleeves can be applied to known nonmedicated, and relatively stable IUD configurations, no modifications of a physician's IUD insertion procedure is necessary. "Relatively stable", as used herein, means that the IUD or platform to which the sleeve is attached is not subject to rapid deterioration or bioerosion in utero, but provides a long-lasting device retaining the medicated sleeve. The closed platform can be a commercially available IUD of known contraceptive effect. The physician can continue to employ the IUD configuration of his choice. The IUD manufacturer need make no modification in the IUD to accommodate or incorporate the drug release article. Dosage or rate of release of drug is a function of the dimensions of the sleeve, and the thickness of the outer covering tube, as well as the amount of drug mixed into the silicone rubber carrier material. Selecting or modifying dosage, then, requires no change in the platform structure.

The foregoing and other advantages of the invention will appear more fully in relation to the following detailed description of a preferred embodiment of the invention, as illustrated in the accompanying drawings.

BRIEF DESCRIPTION OF THE DRAWINGS

FIG. 1 is an enlarged plan view, partially in section, and illustrates an IUD platform carrying a drug-dispensing attachment.

FIG. 2 is a diagrammatic illustration of the steps in the process of making the combination IUD and attachment of FIG. 1.

FIG. 3 is an enlarged side elevational view of a mold and syringe combination for making drug dispensing sleeves to be mounted on existing IUD's.

DESCRIPTION OF PREFERRED EMBODIMENT

Figure 4:
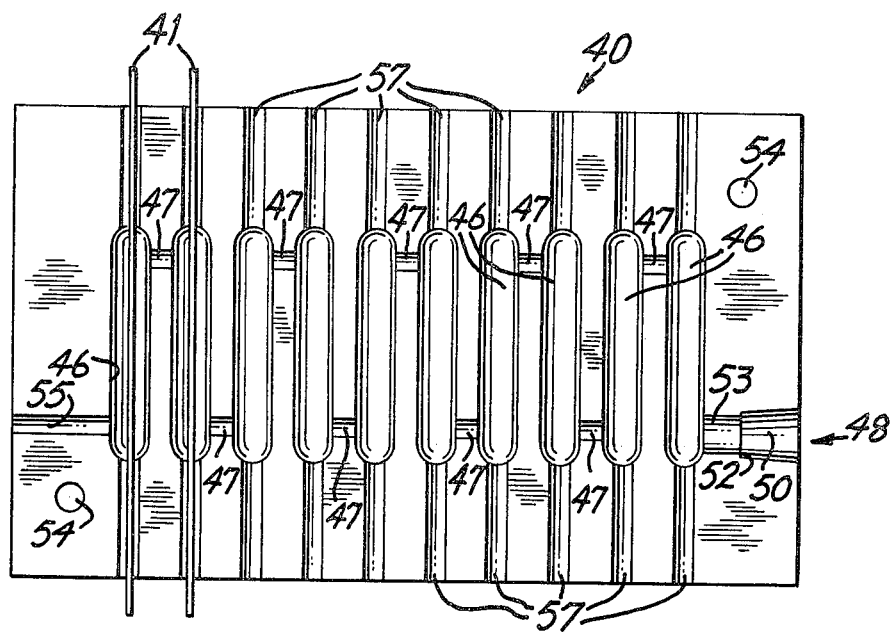
FIG. 4 is a top plan view of one multicavity plate that forms a part of the mold of FIG. 3.

As illustrated in FIG. 1, an existing IUD 11 includes a stem portion 12 that supports a drug-dispensing attachment 15. The attachment includes a sleeve 16 of a carrier or base material such as silicone rubber with a drug evenly distributed throughout. Overlying the sleeve 16, a length of drug permeable tubing 17 tightly fits about the sleeve.

A preferred embodiment of the combination IUD and drug-dispensing attachment of FIG. 1 is made by the method diagrammatically outlined in FIG. 2. First, suitable, medically acceptable, silicone rubber is provided. Room temperature vulcanizing silcione rubber, which is easy to use and readily commercially available, can be prepared by centrifuging the silicone rubber until all filler material has been removed. For example, Medical Grade 382 Silastic, a product of the Dow Corning Corporation, Midland, Mich., has successfully been employed by centrifuging the material for several hours at 100,000 to 200,000 g.

The drug to be dispensed in utero by the attachment 15 is mixed with the silicone rubber. Micronized levonorgestrel was successfully mixed with prepared 382 Silastic by folding the powdered drug into the polymer a little at a time with stirring until a smooth paste of the two components was attained. To assure that the polymer had thoroughly "wet" the drug, the mixture was stirred several times a day for three or four days before use.

Next, the polymer-drug mixture is molded into the form of the sleeve 16 of FIG. 1. To do this, a suitable catalyst is added to the drug-polymer mixture. The mixture is injected into a mold and allowed to cure until solid enough for removal without damaging the sleeves.

Figure 5:
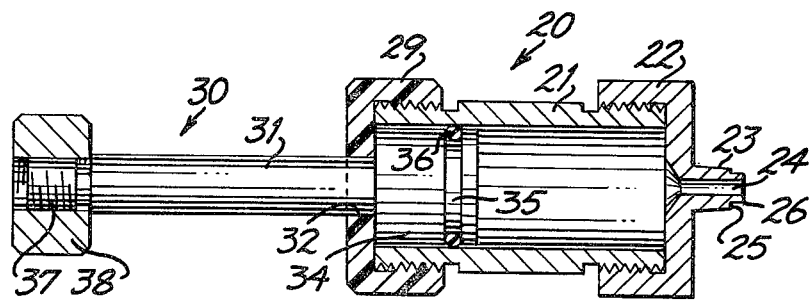
FIG. 5 is a partially sectional view of the syringe of FIG. 3.

A special syringe 20, FIGS. 3 and 5, can be used to inject the viscous polymer and drug mixture into a multicavity mold 40, FIGS. 3 and 4. Both the syringe 20 and the mold 40 are discussed in greater detail below. In the successful example using 382 Silastic silicone rubber and levonorgestrel, Dow Corning Catalyst M, stannous octoate, was the catalyst. This was added and quickly stirred into the mixture of silicone rubber and drug. The syringe was loaded with the catalyzed viscous paste and forced into the mold, using a hydraulic jack to apply pressure. The mixture was allowed to cure for 45 minutes to 1 hour, or until the mixture had become solid enough to allow removal from the mold without damaging the sleeves. The cure time was conveniently judged by testing the hardness of the remnants of the mixture remaining on a Teflon sheet whereon the catalyst and mixture had been mixed.

After curing, the sleeves are removed from the mold. Interconnections formed by the passages in the mold are trimmed away by cutting with a scalpel or razor blade. The mold 40 of FIGS. 3 and 4 employs stainless steel tubes 41 as inserts that define a central opening 18 through the sleeves. Before mounting, the inserts are removed, again with care not to damage the fillerless silicone and drug sleeves. To remove the inserts, the sleeves can be swollen by immersing for a few minutes in a solvent chosen not to dissolve or otherwise adversely affect the silicone rubber or the intermixed drug. The 382 Silastic and levonorgestrel sleeves of the example were swollen in cyclohexane. Similarly, when expanded by solvent, the sleeves are easily mounted by slipping the sleeves onto the stems 12 of the extant IUDs 11.

To slow the rate of release of drug, and to impart greater structural integrity to the attachment, the section of drug permeable tubing 17 can be placed over the sleeve on the IUD. A commercially available silicone rubber tube can be swollen in a non-destructive solvent, and the tubing can be easily slipped onto the sleeve and allowed to shrink in place. In the example described above, Silastic Medical Grade Tubing 602-261 was swollen in cyclohexane for the purpose.

As shown in FIG. 3 and mentioned briefly above, the apparatus for molding the drug-polymer mixture into the form of sleeves 16 includes the specially designed and interfitting syringe 20 and mold 40. Referring to FIG. 5, the syringe includes a hollow, cylindrical, stainless steel body 21. The outer surface of the body 21 is threaded at each end. It receives an interior-threaded stainless steel end cap 22 that has a tapered nipple 23. The nipple is centrally opened by a passage 24. Its outer taper terminates at a shoulder 25 from which projects a slight raised central tip 26.

At its other end, the syringe body 21 receives an internally threaded cap 29 of Delrin, for example. A plunger 30 has a shaft 31 that passes through a closely fitting opening 32 in the cap 29. Within the body 21, the plunger 30 terminates in an enlarged head 34. A peripheral groove 35 seats a sealing O-ring 36 that bears against the interior of the body 21. Remote from the head 34, a reduced, threaded end 37 of the plunger 30 has an internally threaded stainless steel nut 38 secured thereon.

The mold 40 includes two plates 43 and 44 that combine to form the multicavity mold as illustrated in FIG. 3. FIG. 4 shows, in greater detail, the plate 44. Multiple recesses 46 in the face of the plate combine with like recesses 46 in the remaining plate 43 to form the multiple cavities of the mold. A series of grooves 47 forms, with aligned similar grooves 47 in the plate 43, connecting passages between the cavities 46, by which the polymer-drug mixture is conducted from one cavity 46 to the next during injection. Likewise, aligning halves of an injection opening are formed in the plates as shown at 48. The opening has a tapered bore 50, whose taper matches that of the syringe nipple 23. The tapered bore 50 ends in a shoulder 52, beyond which extends a passage 53 that opens into the first cavity 46. Matching alignment holes 54 through the plate facilitate aligning the plates and their cooperating recesses when the mold is closed. From the recess 46 that is farthest from the injection opening 48, a last passage 55 communicates with the exterior of the mold.

Coaxially with each of the recesses 46 and extending from each end thereof, a groove 57 leads from each recess 46 to the mold exterior. Again these are mirrored in the remaining mold plate 43. These grooves locate the inserts 41 that form the central openings in the drug release sleeves. In a preferred embodiment the inserts were stainless steel tubes, but of course they could be pins or other elongate members of a suitable material and of a width satisfactory to provide an opening through the sleeves that will tightly fit onto the stem of the platform.

Returning to FIG. 3, the plates 43 and 44 are shown aligned by pins 58 extending through the alignment openings 54 in the upper and lower plates. The plates are clamped together by any convenient means. C-clamps 59 are shown in FIG. 3, but it will be recognized that any clamping arrangement can be used, including for example bolting the plates together through aligned apertures. In the preferred embodiment the plates were formed of Delrin. Other suitable materials will be apparent to those skilled in the art.

In use, the cavity within the syringe 20 is filled with the drug-polymer mixture after the catalyst has been added to the mixture. The syringe is closed, the nipple 23 is inserted into the injection opening 48, and pressure is applied to the nut 38 at the end of the syringe plunger 30 by, for example, a hydraulic jack. The matching tapers of the stainless steel nipple 23 on the syringe and in the Delrin injection opening bore 50 in the mold produce substantially leak-free mating of the two parts.

In the example discussed above, equal parts by weight of the polymer, Medical Grade 382 Silastic, and the steroid levonorgestrel, were mixed as described, by folding the powdered drug into the polymer a little at a time with stirring to form a smooth paste. The repeated stirring over the course of several days followed. The mold 40 was provided with cavities 46 and inserts 41 having dimensions to give a sleeve length approximately $\frac{3}{4}"$ (actually 18 mm), an outside diameter of about $\frac{1}{8}"$ (3.175 mm), and an opening down the center of about 0.060" (1.5 mm).

Six grams of the drug-polymer mixture was weighed onto a sheet of Teflon and 15 mg of the Dow Corning Catalyst M (stannous octoate) was quickly stirred into the mixture. The catalyst mixture was loaded into the special syringe 20. This was injected into the clamped-closed mold and allowed to cure for 45 minutes to 1 hour. The hardness of the remnants of the mixture remaining on the Teflon sheet, at that time, indicated sufficient curing.

When the mold was opened, the result was a "christmas tree" of sleeves interconnected with each other at alternate ends by the short sections of cured mixture formed in the passages 47 of the mold. The sleeves were separated by cutting the interconnections. The sleeves were swollen in cyclohexane and the tubular inserts 41 were removed. The ends of the sleeves were rounded to present a smooth surface to the endometrium of the uterus.

Using cyclohexane the sleeves were swollen, slipped onto the IUD stem and permitted to shrink thereon, again as described above. Lengths of the Silastic Medical Grade Tubing 602-261, sufficiently long to cover the length of the sleeve on the stem, were provided. This tubing had a 0.095" (2.41 mm) outside diameter and a 0.078" (1.98 mm) inside diameter. The wall thickness was thus 0.0085" (0.22 mm). As described above, the tubing was swollen in cyclohexane, placed over the sleeve on the stem, and allowed to dry and contract.

The drug release sleeve of the example was tested in vitro, and 20 to 25 mcg of levonorgestrel was delivered per day from the sleeve to the surrounding water. In one instance, in vivo testing indicated an average 10.5 mcg per day of the levonorgestrel delivered to the human uterus during a period of 287 days. This same device was then tested in vitro and released 20 mcg per day. The steroid was extracted and it was found that 94% of the original steroid had remained in the device.

In another in vivo test, a drug release device from the same lot as that just described, was in utero for 503 days. Analysis indicated that this device had released an average of 30 mcg per day during its residence in the human uterus.

The variation in extraction of the drug in the two in vivo studies was similar to variations observed in the extraction of levonorgestrel from other types of devices, such as subdermal implants. This is believed to result from the heterogeneous characteristics of the individuals, rather than from any variation in the characteristics of the drug release devices. Variations in the extracting fluids produced in the uterus will vary the rate of extraction of the drug. Levonorgestrel has an atrophic effect, tending to dry the endometrium. While this can slow the release of the drug from the device, this also contributes to the contraceptive effect of the drug, helping to prevent embryo implantation.

Two other sizes of sleeves have been tested, as well. Smaller sleeves, 13 mm long with 3.34 mm diameters, had a total surface area of 136 mm$^2$ each. These were designed to deliver 23 mcg per day of the levonorgestrel. The outer membrane covering provided by the tubing was as described above. Ten of the sleeves were recovered after a mean residence time in utero of 281 days (actual residence times ranged from 98 to 500 days). The amount of levonorgestrel delivered was 22±7 mcg per day (mean±standard deviation). Larger sleeves, 18 mm long with 3.34 mm diameters, had total surface areas of 189 mm$^2$ each, were enclosed in the aforementioned tubing, and gave comparably good results. These larger sleeves were designed to deliver 32 mcg per day of the levonorgestrel. Fourteen were recovered after a mean residence time in utero of 314 days (range 84 to 482 days). The amount of levonorgestrel delivered was 30±9 mcg per day (mean±standard deviation). At the mean rates of release, the attachments just described would be expected to deliver the drug for more than four years.

Dosage can be controlled in several ways. Either or both of the sleeve diameter and length can be adjusted to alter the sleeve surface area. With or without the outer tubing layer, the rate of delivery of drug is a direct function of the total surface area of the sleeve. Reducing the surface area by half, then, will halve the rate of delivery, assuming all other parameters remain the same. Without the outer tubing, the rate of delivery is initially very rapid, giving a "bolus" effect, then declines rather quickly. When the outer tubing is used, the release rate is relatively constant. It is controlled by both the surface area of the sleeve and the wall thickness of the drug permeable tube. For a sleeve of given dimensions, modification of the wall thickness of the silicone rubber tube as described above modifies the release rate, but not in direct proportion to thickness. A doubling of the wall thickness of the tube results in a release rate of about 60% of a single thickness, rather than 50% thereof.

Varying the sleeve and tubing dimensions, provides control of the life as well as the dosage of the sleeves. Long term contraception, as much as seven years, is currently envisioned. Increasing the diameter of the sleeve would allow more drug to be put into the device, and putting on a thicker tube would lower the release rate. Although increasing the diameter would increase the surface area, the thicker tubing would decrease the rate of release per unit of surface. Release rates similar to those described above could thus be achieved plus an increase in effective life.

Placement of the combined device in the uterus is no more difficult than placement of the platform itself. In fact, placement techniques identical to those used with the ordinary, unmedicated IUD's have successfully been employed. No specially formed IUD is necessary. The Nova-T has been preferred as the base platform on which the drug release sleeve is mounted. It is easy to handle, assures that the sleeve will stay in place, and is easily inserted.

In addition to the dosage factors discussed above, the diameter of the sleeve 16 is chosen in connection with the inside diameter of the inserted tube used in placement of the IUD. In the case of the Nova-T platform, the arms fold up and can fit into a very narrow inserter tube. The sleeve diameter, then governs the size of the inserter tube. As can be appreciated from FIG. 1, the sleeve diameter is such that little or no increase is necessary in the diameter of the inserter tube and no difficulty in placement of the IUD and sleeve results.

The combination IUD platform and drug release attachment described above gives good contraceptive benefit. It acts as a known, unmedicated IUD, and as a controlled dosage, directly administering contraceptive drug dispensing device. Another advantage appearing to result from the use of the sleeve described above is a decrease in menstrual blood loss. Drug release intrauterine devices currently on the market appear to give this effect, as well, but with those, higher extra-uterine pregnancy rates have been observed.

Drugs delivered with devices of the kind described above may be any of those useful for treatment of any condition of the uterus or endrometrium thereof, as well as steroids useful in providing contraceptive effects, whether of local or of systemic activity. Although only the room temperature vulcanizing silicone rubber has been used so far in forming the sleeves, many other polymer and drug mixtures will prove useful in forming these. Likewise, only silicone rubber tubing as described above has been used to control the release rate and impart greater structural integrity, but the other membrane, may, as well, be composed of other biocompatible polymers that may be applied in a variety of ways, such as by dip-coating, heat-sealing, spraying, or otherwise.

For the construction of the mold 40, Food-Grade Delrin was chosen, but a suitable mold could be formed of, for example, carbon steel, stainless steel, brass, aluminum, polycarbonates, polyacetates, lucite, Teflon, polyethylene, polypropylene, polysulfone, and other materials of known, suitable strength and ease of manufacture. The same is true as to choice of materials for both the inserts 41 for the mold and the parts of syringe 20.

Any of a number of solvents can be used to swell the silicone rubber and drug sleeve and the silicone rubber tubing. Cyclohexane was chosen for its quickness in swelling these members, the greater extent to which it swells them, and for its safety. However, any of the hexanes, straight-chain parafins, and normal hydrocarbons that are fully saturated should suffice. Again, the solvent should dissolve neither the steroid nor the silicone rubber. In this relation, ether, toluene or chloroform would surely be unsatisfactory.

Although particular preferred embodiments of the IUD platform and attachment, and of the method and apparatus for making the same are described and illustrated herein, many modifications thereof will be apparent to those skilled in the art, without departure from the spirit and scope of the invention as set forth in the appended claims.

We claim:

1. A method of making a combination intrauterine device and drug release attachment comprising:
   (a) providing a nonfiller-containing formable silicone rubber for a carrier material;
   (b) mixing together a drug for in utero administration and a formable carrier material from step (a);
   (c) providing a nonmedicated and relatively stable platform for intrauterine placement;
   (d) forming the mixture of drug and carrier material into an attachment adapted to fit onto the platform;
   (e) mounting the attachment on the platform structure for controlled release of the drug in utero; and
   (f) said mounting including expanding the attachment by immersion in a solvent suitable for swelling the polymer and in which the polymer and the drug are substantially insoluble, and shrinking the expanded attachment about a portion of the platform.

2. The method according to claim 1 wherein the step of providing a nonfiller-containing formable silicone rubber further comprises providing a formable silicone rubber containing a filler and removing the filler from the silicone rubber prior to mixing with the drug to enhance in utero drug release by the attachment.

3. A method according to claim 2 further comprising the step of placing a drug permeable covering over the attachment whereby the administered drug is controlled as a function of the thickness of the covering.

4. The method according to claim 1 or 2, wherein the step of forming further includes providing a pair of plates with aligned multiple recesses therein to define the multiple cavities of the mold, securing the plates together with the recesses in alignment, locating elongate central opening forming members in the cavities defined by the recesses to establish central axial openings through the molded sleeves, separating the plates after the carrier and drug mixture has set, and trimming undesired portions from the sleeves prior to application to the intrauterine platforms.

5. The method according to claim 1 or 2, wherein the step of forming includes defining an opening through the attachment, and the step of mounting includes temporarily expanding the attachment with the solvent, placing a stem of the intrauterine platform through the opening for subsequent shrinkage of the attachment about the stem.

6. The method according to claim 1 or 2, wherein the polymer is a silicone rubber and the solvent is cyclohexane.

7. The method according to claim 2, wherein the step of removing the filler from the silicone rubber includes centrifuging the silicone rubber prior to mixing the drug and silicone rubber.

8. The method according to claim 1 or 2, wherein the step of forming includes loading a syringe with a quantity of the mixture of carrier material and drug, and injecting the quantity into a multicavity mold to mold attachments in the form of sleeves dimensioned to fit on a plurality of the preexisting intrauterine platforms.

9. The method according to claim 2, wherein the filler removed from the silicone rubber is a reinforcing material for adding structural integrity to the formed silicone rubber, and the method further includes the step of placing an outer drug permeable covering in tightly fitting and reinforcing relation over the attachment.

10. The method according to claim 9, wherein the step of placing an outer covering includes shrinking a length of preformed tubing tightly about the attachment on the intrauterine platform.

11. A method according to claim 1 further comprising the step of placing a drug permeable covering over the attachment whereby the administered drug is controlled as a function of the thickness of the covering.

12. The method according to claim 11 or 3, wherein the step of placing the covering comprises temporarily expanding a length of drug permeable tubing, and placing the tubing over the attachment for subsequent shrinkage of the tubing about the attachment.

13. The method according to claim 6, wherein the tubing is a polymer and the step of expanding includes immersing the tubing in a solvent suitable for swelling of the polymer absent dissolving thereof.

* * * * *

UNITED STATES PATENT AND TRADEMARK OFFICE
CERTIFICATE OF CORRECTION

PATENT NO. : 4,341,728
DATED : July 27, 1982
INVENTOR(S) : Robertson et al.

It is certified that error appears in the above—identified patent and that said Letters Patent is hereby corrected as shown below:

<u>First page</u>, the following sentence should be added to the end of the ABSTRACT: --The syringe is made especially for use with the mold.--
<u>Col. 10, line 16</u>, "claim 6" should read --claim 12--.

Signed and Sealed this

Sixteenth Day of November 1982

[SEAL]

Attest:

GERALD J. MOSSINGHOFF

Attesting Officer     Commissioner of Patents and Trademarks